United States Patent [19]
Nakayama et al.

[11] Patent Number: 5,998,198
[45] Date of Patent: Dec. 7, 1999

[54] MICROORGANISMS THAT DECOMPOSE HALOGENATED HYDROCARBONS AND THEIR USE

[75] Inventors: Mika Nakayama, Kasugai; Chie Miyazaki, Nisshin; Osamu Asami, Konan; Yukio Yamada, Tsushima; Koichi Numata, Nagoya; Yasushi Oda, Toyota, all of Japan

[73] Assignee: Toyota Jidosha Kabushiki Kaisha, Toyota, Japan

[21] Appl. No.: 08/981,352

[22] PCT Filed: Apr. 18, 1997

[86] PCT No.: PCT/JP97/01359

§ 371 Date: Dec. 19, 1997

§ 102(e) Date: Dec. 19, 1997

[87] PCT Pub. No.: WO97/40136

PCT Pub. Date: Oct. 30, 1997

[30] Foreign Application Priority Data

Apr. 22, 1996 [JP] Japan .................................. 8-100466

[51] Int. Cl.$^6$ ...................................................... B09B 3/00
[52] U.S. Cl. .................................... 435/262.5; 435/252.1; 435/253.3; 435/874
[58] Field of Search ........................... 435/252.5, 252.34, 435/874, 252.1, 253.3

[56] References Cited

FOREIGN PATENT DOCUMENTS

WO 9219738  12/1992  WIPO .

OTHER PUBLICATIONS

Nelson et al., *Appl. Env. Microbiol.*, 53:5, pp. 949–954, 1987.

Shields et al., *Appl. Evn. Microbiol.*, 57:7, pp. 1935–1941, 1991.

Shields et al., *Appl. Env. Microbiol.*, 58:12, pp. 3977–3983, 1992.

Luu et al., *Appl. Microbiol. Biotechnol.*, vol. 44, pp. 259–264, 1995.

Rogers, B. et al.: "Degradation of trichloroethylene sorbed to soil and clay sorbents by *Burkholderia cepacia* strains G4 and PC5.", & 96th General Meeting of the American Society for Microbiology, New Orleans, Ouisiana, USA, May 19–23, 1996. Biological Abstracts, vol. 98, Philadelphia, PA, US.

Mars, Astrid E. et al.: "Degradation of toluene and trichlorethylene by *Burkholderia cepacia* G4 in growth–limited fed–batch culture" & Appl. Environ. Microbiol. (1996), Chemical Abstracts, vol. 124, No. 14, Apr. 1, 1996.

Leahy, Joseph G. et al.: Comparison of factors influencing trichloroethylene degradation by toluene–oxidizing bacteria: & Appl. Environ. Microbiol. (1996) Chemical Abstracts, vol. 124, No. 15, Apr. 9, 1996.

Shields, M.S. et al.: "Tom, a new aromatic degradative plasmid from *Byrkholderia* (Pseudomonas) *cepacia* G4" & Appl. Environ. Microbiol. (1995) Chemical Abstracts, vol. 122, No. 23, Jun. 5, 1995.

Winkler, Joerg et al.: "Tracking the response of *Byrkholderia cepacia* G45223–PRI in aquifer microcosms" & Appl. Environ, Microbiol. ('995) Chemical Abstracts, vol. 122, No. 12, Mar. 20, 1995.

Munakata–Marr, Junko et al.: "Trichloroethylene oxidation by puriified toluene 2–monooxygenaase: products, kinetics, and turnover–dependent inactivation" & J. Bacteriol. (1997)Chemical Abstracts, vol. 124, No. 20, May 13, 1996.

Newman, Lisa M. et al.: trichloroethylene oxidatiion by purified toluen 2–monooxygenase: products, kinetics, and turnover–dependent inactivation : &J.Bacteriol (1997) Chemical Abstracts, vol. 126, No. 9, Mar. 3, 1997.

Matheson, V.G. et al.: "Use of strain–specific nucleic acid probes to assess remediation of an aquifier contaminated with trichloroethylene by bioaugmentation with *Burkholderia cepacia* G4" & MEDED. —Fac. Landbouwkd. Toegepaste Biol. Wet. (Univ. Gent) (1996, Chemical Abstracts, vol. 125, No. 24 Dec, 9, 1996.

Asami, Osamu et al.: "Pseudomonas for degradation of halogenated hydrocarbons" & JP 09 149 786 A (Toyota Central Research and Development Laboratories, Inc. Japan) & Chemical Abstracts, vol. 127, Columbus,Ohio, US.

*Primary Examiner*—David A. Redding
*Attorney, Agent, or Firm*—Kenyon & Kenyon

[57] ABSTRACT

Microorganisms belonging to the genus Burkholderia and having the ability to decompose halogenated hydrocarbon, which are able to decompose 50% or more of 100 ppm of trichloroethylene in 2 days, or decompose 100% of 30 ppm of trichloroethylene in 18 hours, as well as providing a process for decomposing halogenated hydrocarbons in water or soil using those microorganisms.

9 Claims, 5 Drawing Sheets

MICROORGANISMS THAT DECOMPOSE HALOGENATED HYDROCARBONS AND THEIR USE

TECHNICAL FIELD

The present invention relates to a biocleaning process for water or soil contaminated by halogenated hydrocarbon.

BACKGROUND ART

Recently, organic solvents, and particularly halogenated hydrocarbons, have been used in large amounts as cleaners and so forth in advanced industries. Since growing attention is being focused on contamination of groundwater and soil caused by these substances or waste water containing these substances, there is a desire to implement countermeasures against this contamination immediately.

Examples of known physical methods that have been employed in the past as countermeasures include an air stripping method in which the contaminated soil is excavated and air is blown through the soil to volatilize the halogenated hydrocarbons and adsorb it with activated charcoal and so forth, and a vacuum extraction method in which the contaminated soil is pounded into a pipe after which a vacuum is drawn to aerate the soil and remove the contaminants. These methods are considered to be able to be applied to decontamination of groundwater as well.

However, these methods have the disadvantage of requiring a large amount of energy, such as for blowing in air. In addition, the former has the disadvantage of requiring that the soil be excavated, while the latter has the disadvantage of extraction efficiency decreasing as the concentration of contaminant decreases, thus making the cleaning difficult. Moreover, from the viewpoint of preventing secondary contamination such as air pollution, these methods require that separate contaminants be detoxified in order to adsorb onto activated charcoal and so forth.

On the other hand, research has been conducted in recent years on so-called biocleaning methods in which contaminants are efficiently decomposed and detoxified by microorganisms. Since these methods utilize the decomposition mechanism of microorganisms, they do not require a large amount of energy as compared with the above-mentioned physical methods. They are also able to completely decompose and detoxify contaminants without causing secondary contamination. Moreover, the cleaning can be performed even at low concentrations of contaminants, thus enabling decontamination to be performed over a wide area at the original location and creating significant expectations of low costs.

Examples of methods used to purify contaminated soil by microorganisms include a solid phase treatment in which microorganisms are mixed into excavated soil with nutrient sources such as phosphorous and nitrogen to promote decomposition of contaminants, a slurry treatment in which microorganisms are mixed into excavated soil with water and nutrient sources to treat the soil in the liquid state and promote decomposition of contaminants, and an original location treatment in which air, nutrient sources and so forth are injected into contaminated soil without excavating to promote decomposition of contaminants by microorganisms present in the soil.

Among the above-mentioned biotreatment techniques, since soil excavation is required and the application range is limited in the case of the solid phase treatment and slurry treatment method, treatment and equipment costs are relatively high.

On the other hand, the original location treatment method involves relatively low costs and allows treatment over wide area. However, the cleaning rate is slow since the the absolute number of soil microorganisms is low. In the case of compounds that are difficult to decompose such as halogenated hydrocarbons in particular, there is a possibility that microorganisms being able to decompose contaminants in the soil may not be present in the soil, thus making cleaning impossible. In this case, acquiring microorganisms that are able to decompose halogenated hydrocarbons and inoculating them into the soil enables the cleaning rate to be improved and soil to be purified even though microorganisms being able to decompose the contaminants are not present in the soil.

A halogenated hydrocarbon contaminant, trichloroethylene (TCE), is widely used in the IC industry, in dry cleaning and so forth. It is particular important as a contaminant since it is reported to be carcinogenic. Known examples of microorganisms that decompose TCE include the methane assimilating microorganisms *Methyrosinus tricosiorium* OB3 (Japanese Unexamined Patent Publication No. 4-501667, Japanese Unexamined Patent Publication No. 5-212371) and *Methyrosinus tricosporium* TUKUBA (Japanese Unexamined Patent Publication No. 2-92274 and Japanese Unexamined Patent Publication No. 3-292970), Pseudomonas, such as *Pseudomonas putida* F1 (Japanese Unexamined Patent Publication No. 64-34499), *Pseudomonas putida* BH (Fujita, et al., Chemical Engineering, 39, (6), p.494–498, 1994), *Pseudomonas putida* UC-R5 and UC-P2 (Japanese Unexamined Patent Publication No. 62-84780), *Pseudomonas putida* KWI-9 (Japanese Unexamined Patent Publication No. 6-70753), *Pseudomonas mendocina* KR-1 (Japanese Unexamined Patent Publication No. 2-503866 and 5-502593), *Pseudomonas cepacia* G4 (Japanese Unexamined Patent Publication No. 4-502277) and *Pseudomonas cepacia* KK01 (Japanese Unexamined Patent Publication No. 6-296711) and other microorganisms such as *Alcaliaenes eutronus* JMP134 (A. R. Harker, Appl. Environ. Microbiol., 56, (4), 1179–1181, 1990), *Alcaliaenes eutropus* KS01 (Japanese Unexamined Patent Publication No. 7-123976), and the ammonia bacteria *Nitrosomonus europaea* (D. Arciero, et al., Biochem. Biophys. Res. Commun., 159, (2), 640-643, 1989) are known.

*Pseudomonas cepacia* KK01 in particular is reported to decompose TCE at an initial concentration of 30 ppm to a concentration of 15 ppm in liquid culture, and TCE in soil having an initial concentration of 5 ppm to a concentration of 1 ppm (Japanese Unexamined Patent Publication No. 6-296711). In addition, *Alcaliaenes eutropus* KS01 is reported to have the ability to decompose TCE at a concentration of 50 ppm in a liquid culture to a concentration below the detection limit, and decompose TCE in the soil at 1 ppm below the detection limit (Japanese Unexamined Patent Publication No. 7-123976).

However, when testing the decomposing abilities of these microorganisms, decomposition is demonstrated at extremely high cell concentrations ($1 \times 10^8$ cells/ml) in all cases. When considering that this concentration is unrealistic in the actual soil environment, the decomposing abilities of these microorganisms is not always considered to be high. Thus, in the case of using microorganisms for soil cleaning, the microorganisms have sufficient decomposing ability and are able to demonstrate that ability in the special environment of the soil, such as in the presence of wild microorganisms. In addition, it is preferable that the tolerance of the microorganisms to TCE, the target of decomposition, be high, and that they also have the ability to decompose dichloroethylene (DCE), which is a partial decomposition product of TCE.

Disclosure of Invention

The object of the present invention relates to microorganisms that efficiently decompose halogenated hydrocarbons, and particularly high concentrations of TCE, DCE and so forth, as well as a cleaning process for water or soil that uses those microorganisms.

The present invention provides microorganisms having the ability to decompose halogenated hydrocarbon and belonging to the genus Burkholderia, and some of those microorganisms belonging to the species *Burkholderia cepacia*. Examples of these microorganisms include Burkholderia N16-1 (FERM BP-5504), *Burkholderia cepacia* N15-1 (FERM BP-5502) and *Burkholderia cepacia* N15-2 (FERM BP-5503). Moreover, the present invention provides a process for cleaning water or soil where the above-mentioned microorganisms are added to water or soil containing halogenated hydrocarbon.

The present invention is also characterized by the addition of microorganism activator in combination with the above-mentioned microorganisms. These microorganisms have the ability to decompose 50% or more of 100 ppm of trichloroethylene in 2 days, or to decompose 100% of 30 ppm of trichloroethylene in 18 hours.

DETAILED DESCRIPTION

Figure 1:
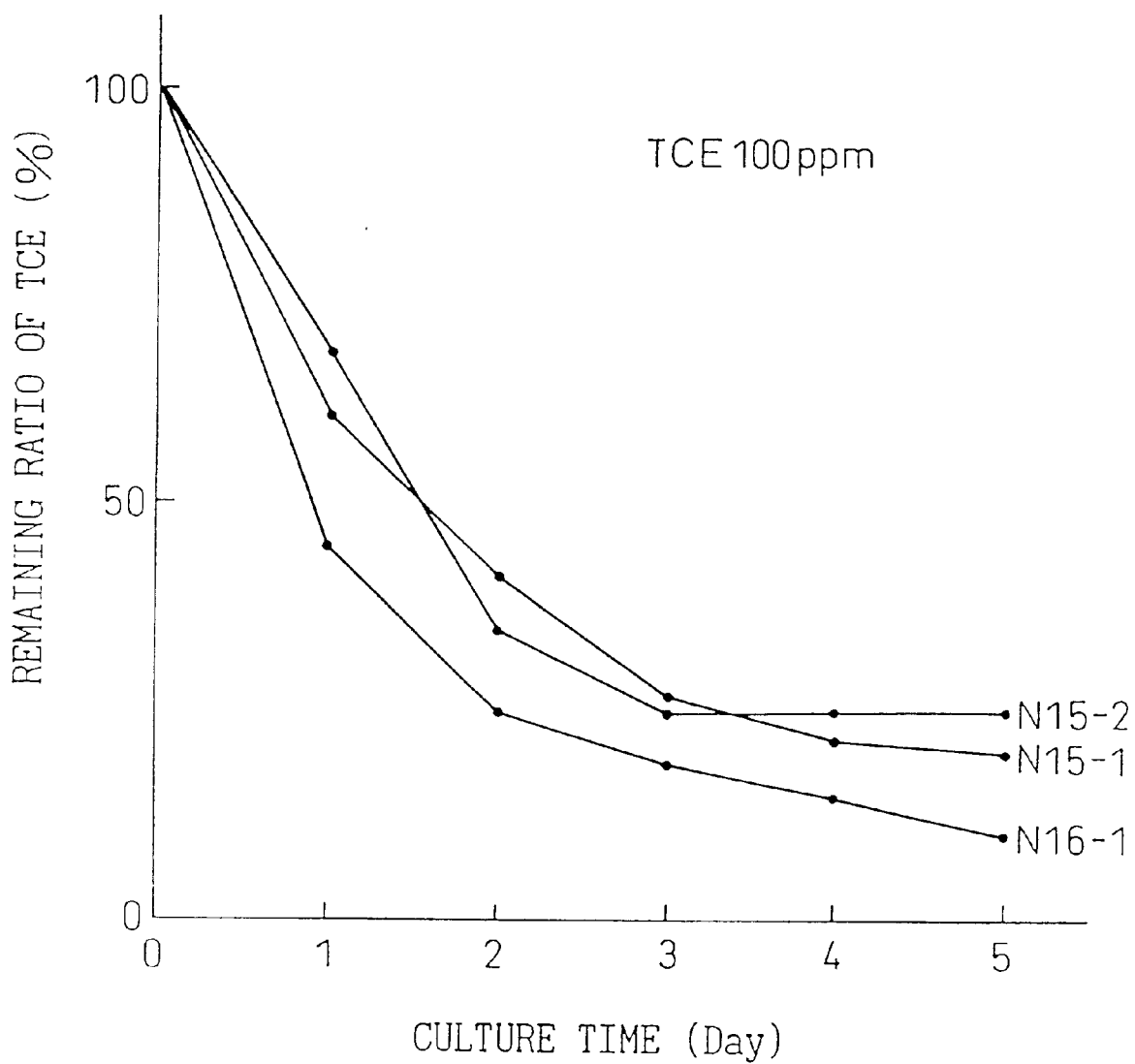
FIG. 1 is a graph indicating the change over time in the percentage of remaining TCE in Example 2.

The microorganisms of the present invention should be microorganisms belonging to the genus Burkholderia or microorganisms belonging to the species *Burkholderia cepacia*, specific examples of these microorganisms include Burkholderia N16-1, *Burkholderia cepacia* N15-1 and *Burkholderia cepacia* N15-2. These microorganisms are new strains isolated from nature such as rivers and soil, and their isolation method and taxonomical characteristics are specifically described. These strains, Burkholderia N16-1, *Burkholderia cepacia* N15-1 and *Burkholderia cepacia* N15-2 were deposited on Apr. 12, 1996 with the National Institute of Bioscience and Human Technology Agency of Industrial Science and Technology as FERM BP-5504, FERM BP-5502 and FERM BP-5503, respectively.

The microorganisms of the present invention can be cultured in the presence of routinely used carbon sources and nitrogen sources in a medium containing inorganic salt, vitamins and other trace elements as necessary. Any carbon source can be used provided it is a carbon source that is preferentially assimilated by the microorganisms of the present invention. Although varying according to the type of carbon source, the concentration of carbon source in the medium is preferably, for example, 0.1 to 0.5 g/L. Examples of nitrogen sources that can be used include organic nitrogen sources such as yeast extract, peptone and meat extract, while examples of inorganic nitrogen sources include ammonium salts and nitrates.

Although varying according to the particular type, the concentration of the nitrogen source is preferably 0.1 to 1.4 g/L. Preferable examples of inorganic salts include those composed of metal ions such as potassium, calcium, magnesium, iron (II), manganese, cobalt and nickel ions, and anions such as chloride, sulfate and phosphate ions. Culturing is preferably performed aerobically, and aeration and stirring are preferable in the case of shake culturing or large-scale culturing. The culture temperature is 20 to 37° C. and preferably around 30° C.

In addition, the present invention relates to a process for cleaning water or soil characterized by adding the above-mentioned microorganisms to water or soil containing halogenated hydrocarbon. In this process, the microorganisms of the present invention cultured in the manner described above should be added to the water or soil to be treated. The microorganisms may be added in the form of a culture liquid or added in the form of microorganisms after isolating from a culture liquid. Moreover, the microorganisms may also be added after adsorbing onto a separate carrier.

Although the amount of microorganisms added varies according to the halogenated hydrocarbon decomposition ability of the microorganisms, the amount of halogenated hydrocarbon in the water or soil to be treated and so forth, it is within the range of $10^5$ to $10^9$ cells/g. Although the time required for treatment also varies according to the halogenated hydrocarbon decomposition ability of the microorganisms used, the amount of halogenated hydrocarbon in the water or soil to be treated and the amount of microorganisms added, it is approximately 1 to 10 days.

In addition, the cleaning process for water or soil of the present invention relates to a process for cleaning water or soil in which the microorganisms of the present invention as described above are inoculated into water or soil contaminated by halogenated hydrocarbon and mixed to decompose the halogenated hydrocarbon contained in the water or soil, and is characterized by the addition and mixing of at least one type of microorganism activator during inoculation and mixing of the above-mentioned microorganisms in the above-mentioned water or soil. In this case, the microorganism activator has the role of activating the halogenated hydrocarbon decomposition ability of the microorganisms, and is referred to as an inducer. Examples of inducers that can be used include compounds that can be assimilated and decomposed by the above-mentioned microorganisms, preferable examples of which include benzene, toluene, phenol, cresol and 3-hydroxybenzyl alcohol. In addition, cyclopentanol, hexanoic acid, trans-3-hexenoic acid and suberinic acid can be used for N16-1 in addition to the inducers indicated above.

Examples of halogenated hydrocarbons that can be decomposed by the process of the present invention are particularly chlorinated hydrocarbons such as TCE, DCE and monochloroethylene.

Although the process of the present invention can be applied to the solid phase treatment method and slurry treatment method previously described, it is not always necessary to use these methods that require excavation of the soil, but rather cleaning can be performed simply by adding and inoculating the microorganisms of the present invention into the soil or water.

EXAMPLES

The following provides a detailed explanation of the present invention through Examples.

Example 1. Isolation and Identification of Microorganisms

Microorganisms of the present invention were screened and isolated from-the soil on the grounds of a chemical plant using the method described below. 0.1 g of sampled soil were inoculated into 5 ml of NMS medium or M9 medium in a 25 ml screw-top test tube. Moreover, 500 ppm of phenol and vitamin cocktail was added, after which the tube was capped and cultured with shaking for a prescribed time at 30° C. Culturing was continued until culture medium became cloudy due to microorganism growth in the medium. After completion of 10 rounds of subculturing, the culture liquid was suitably diluted and swabbed onto plate medium to which 1.5% agar was added to isolate the microorganism colonies that appeared. The microorganisms were isolated by repeating this procedure.

TABLE 1

| Composition of NMS Medium (in 1 Liter) | |
| --- | --- |
| $MgSO_4 \cdot 7H_2O$ | 1.0 g |
| CaC12 | 0.01 g |
| $Na_2HPO_4 \cdot 12H_2O$ | 0.717 g |
| $NH_4Cl$ | 0.6 g |
| $KH_2PO_4$ | 0.272 g |
| Trace element solution (pH 6.8.) | 0.5 ml |
| Trace Element Solution (in 1 Liter) | |
| EDTA | 500 mg |
| $FeSO_4 \cdot 7H_2O$ | 200 mg |
| $ZnSO_4 \cdot 7H_2O$ | 10 mg |
| $MnCl_2 \cdot 4H_2O$ | 3 mg |
| $H_3BO_3$ | 30 mg |
| $CoCl_2 \cdot 6H_2O$ | 20 mg |
| $NiCl_2 \cdot 6H_2O$ | 2 mg |
| $CaCl_2$ | 1 mg |
| $Na_2MoO_4 \cdot 2H_2O$ | 2 mg |
| Vitamin Cocktail (in 1 Liter) | |
| Thiamine hydrochloride | 3 mg |
| p-aminobenzoic acid | 13 mg |
| Adenine | 1.0 g |
| NAD | 0.25 g |
| Vitamin $B_{12}$ | 10 mg |
| Thiamine diphosphochloride | 100 mg |

After culturing the isolated microorganisms in the liquid medium for 2 days, 1/100th volume of the culture liquid was inoculated into a 30 ml vial containing 4 ml of NMS medium to which phenol, 0.02% yeast extract and 1 mM glucose, had been added, followed by the addition of 10 ppm of TCE. After promptly sealing the vial with a Teflon-coated septum cap and aluminum cap and shake culturing for 5 days at 30° C., the vapor phase in the vial was analyzed by gas chromatography. The morphological and physiological properties of the three strains of microorganisms having a high degree of TCE decomposition activity that were selected in this manner were investigated. Those results are shown in Table 2.

TABLE 2

| | Test Results | | |
| --- | --- | --- | --- |
| Test Parameter | N15-1 | N15-2 | N16-1 |
| Morphology | Rod | Rod | Rod |
| Gram staining | − | − | − |
| Spores | − | − | − |
| Motility | + | + | + |
| Flagella | Polar, multi-flagellate | Polar, multi-flagellate | Polar, multi-flagellate |
| Response to oxygen | Aerobic | Aerobic | Aerobic |
| Oxidase | + | + | + |
| Catalase | + | + | + |
| OF | O | O | O |

TABLE 2-continued

| | Test Results | | |
| --- | --- | --- | --- |
| Test Parameter | N15-1 | N15-2 | N16-1 |
| Colony color tone | NP | NP | NP |
| Fluorescent pigment formation | − | − | − |
| Water-soluble pigment formation | − | − | − |
| PHB accumulation | + | + | + |
| Cleavage of protocatechinic acid | Ortho form | Ortho form | Ortho form |
| Arginine dihydrolase | − | − | − |
| Growth at 40° C. | + | + | − |
| Denitrification reaction | − | − | − |
| Nitrate reduction | + | + | − |
| Gelatin liquefaction | + | + | − |
| Starch decomposition | − | − | − |
| Assimilation | | | |
| Glucose | + | + | + |
| Xylose | + | + | + |
| Rhamnose | − | − | + |
| Levulinic acid | + | + | − |
| Mesaconic acid | − | − | − |
| D-tartaric acid | − | − | + |
| 2,3-butylene glycol | + | + | − |
| Tryptamine | − | − | − |
| Quinone type | Q-8 | Q-8 | Q-8 |
| GC content of intracellular DNA (mol %) | 66 | 67 | 62 |

As a result of identifying the above-mentioned microorganisms from the above results according to the literature (N. R. Krieg and J. G. Holt, "Bergey's Manual of Systematic Bacteriology", Vol. 1 (1984) Williams & Wilkins; J. G. Holt, N. R. Krieg, P. H. A. Sneath, J. T. Staley and S. T. Williams, "Bergey's Manual of Determination Bacteriology", Ninth Edition (1994) Williams & Wilkins; N. Zhao, C. Qu, E. Wang and W. Chen, Int. J. Syst. Bacteriol., 45, 600 (1995); E. Yabuuti, Y. Kosako, H. Oyaizu,. I. Yano, H. Hotta, Y. Hashimoto, T. Ezaki and M. Arakawa, Microbiol. Immunol., 36, 1251 (1992)), one strain is was identified as Burkholderia species, while the other two strains were identified as *Burkholderia cepacia*, and were named N16-1, N15-1 and N15-2, respectively.

Known microorganisms that decompose TCE belonging to the species *Burkholderia cepacia* are G4 (Japanese Unexamined Patent Publication No. 4-502277) and KKO1 (Japanese Unexamined Patent Publication No. 6-296711) as previously described. Since both N15-1 and N15-2 have motility as shown in Table 4, they are clearly different from G4 which is not motile. In addition, although G4 and KK01 are induced by toluene, since N15-1 and N15-2 are not induced by toluene, they are clearly different based on this parameter as well. On the other hand, since N16-1 has an intracellular DNA GC content of 62 mol% and does a not fall under *Burkholderia putida, mendocina* or *cepacia* that are known to be microorganisms that decompose TCE (previously classified as a Pseudomonas species prior to 1992), it was certified as a novel microorganism.

Example 2. Decomposition of TCE in Liquid Medium

Strains N15-1, N15-2 and N16-1 were cultured for 1 day each in NMS liquid medium to which 500 ppm of phenol and vitamin cocktail had been added. After collecting the microorganisms by centrifugation, the microorganisms were resuspended in 4 ml of the same medium not containing phenol. 30 ml of this suspension were transferred to vials followed by the addition of 100 ppm of TCE after which the vials were promptly sealed with a Teflon-coated silicon septum and aluminum cap (microorganism concentration: $10^8$ cells/ml). The vials were then cultured by allowing to stand undisturbed at 30° C. The vapor phase was periodically analyzed by gas chromatography. Those results are shown in FIG. 1. More than 70% of the TCE in the culture liquid was decomposed in 5 days by each of the microorganisms.

Example 3. Decomposition of TCE in Liquid Medium

Figure 2:
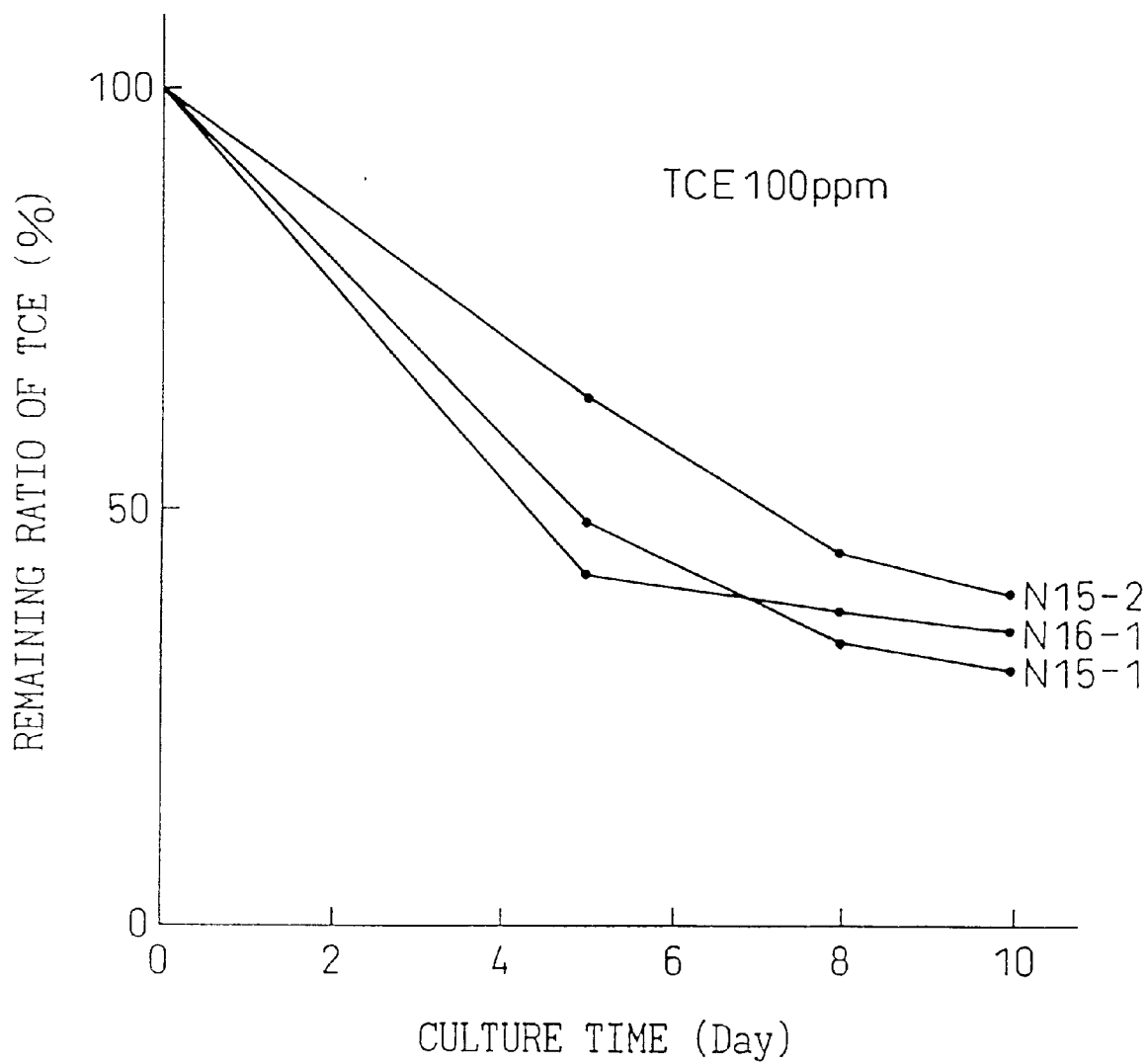
FIG. 2 is a graph indicating the change over time in the percentage of remaining TCE in Example 3.

Strains N15-1, N15-2 and N16-1 were cultured for 1 day each in NMS liquid medium to which 0.2% yeast extract and 4 mM glucose had been added. 4 ml of NMS liquid medium to which 0.02% yeast extract, 500 ppm of phenol and 1 mM glucose had been added was placed in vials and inoculated with 40 $\mu$l each of the above-mentioned culture liquid (microorganism count of roughly $10^6$ cells/ml). 100 ppm of TCE were then added followed by promptly sealing the vials with a Teflon-coated silicon septum and aluminum cap. The vials were incubated with shaking at 30° C., and the vapor phase was periodically analyzed by gas chromatography. Those results are shown in FIG. 2.

More than 60% of the TCE in the culture liquid was decomposed by each of the microorganisms in 10 days. When this decomposing ability was compared with known TCE-decomposing microorganisms, there were only two reports describing TCE in excess of 30 ppm. Of those, *Pseudomonas cepacia* KK01 (Japanese Unexamined Patent Publication No. 6-296711) was reported to have the ability to decompose 30 ppm of TCE down to roughly 15 ppm (50%) in 2 days, while *Alcaligenes eutropus* KS01 was reported to be able to decompose 50 ppm of TCE to a level below the detection limit of gas chromatography in 4 days at a microorganism concentration of $10^8$ cells/ml. In comparison, since N15-1, N15-2 and N16-1 are able to decompose TCE at a concentration as high as 100 ppm while also having a high decomposing ability per cell, in addition to being able to accommodate a broader range of contamination concentrations at the time of actual use, and since the amount of microorganisms required can be drastically reduced, they also offer the advantage of being able to decrease costs.

Example 4. Decomposition of DCE in Liquid Medium

Figure 3:
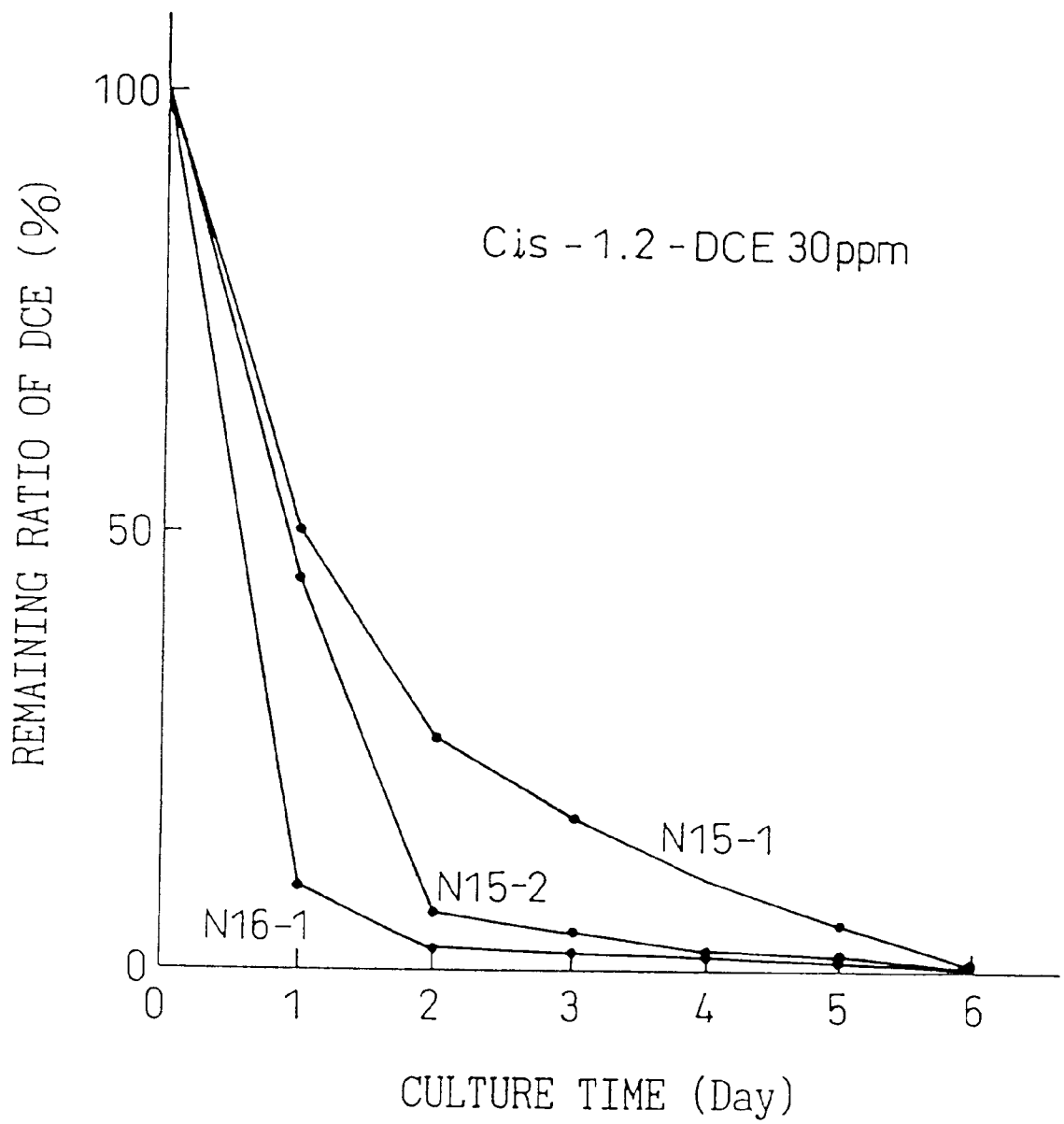
FIG. 3 is a graph indicating the change-over time in the percentage of remaining cis-1,2-DCE in Example 4.

Strains N15-1, N15-2 and N16-1 were each inoculated into 5 ml of NMS liquid medium to which 0.02% yeast extract, 500 ppm phenol and 1 mM glucose had been added. After culturing for 2 days at 30° C., 1/100th volume of the culture liquid was added to a vial containing 4 ml of the same culture liquid containing 30 ppm cis-1,2-DCE, followed by culturing for 5 days at 30° C. The results are shown in FIG. 3. Decomposition of more than 99% of the DCE was observed for all three strains.

Example 5. Effect of Temperature During Decomposition

Strains N15-1, N15-2 and N16-1 were each inoculated into 5 ml of NMS liquid medium to which 0.02% yeast extract, 500 ppm phenol and 1 mM glucose had been added. After culturing for 2 days at 30° C., 1/100th volume of the culture liquid was added to vials containing 4 ml of the same culture liquid to which had been added 30 ppm of TCE, followed by culturing for 8 days at 16 to 30° C. In the cases of N16-1 and N15-1, TCE was decomposed below the detection limit at each temperature. In the case of N15-2, however, although approximately 30% of the TCE remained at 16° C., the amount was below the detection limit at 20° C. and above. Accordingly, it was shown that these microorganisms are able to decompose TCE at the temperature (15 to 20° C.) of the soil.

Example 6. Effect of pH During Decomposition

Strains N15-1, N15-2 and N16-1 were each inoculated into 5 ml of M9 liquid medium (pH 7.0) to which 0.02% yeast extract, 500 ppm phenol and 1 mM glucose had been added. After culturing for 2 days at 30° C., 1/100th volume of the culture liquid was added to vials containing 4 ml of culture medium adjusted to a pH of 5-10, and to which had been added 30 ppm of TCE instead of phenol, followed by culturing for 5 days at 30° C. N15-1, N15-2 and N16-1 each decomposed 30 ppm TCE to a level below the detection limit at all pH levels. In addition, although the growth of N16-1 was inhibited at pH level of 7.4 and above, it decomposed TCE to a level below the detection limit in the pH range of 5 to 7.

Example 7. Decomposition Test of TCE in Soil 10 g of Andsols (sampled from Aichi prefecture and air dried) were placed in a vial having a volume of 30 ml followed by the addition of TCE to a concentration of 20 ppm. Strains N15-1, N15-2 and N16-1 were each inoculated into 20 ml of NMS liquid medium to which 0.02% yeast extract, 500 ppm phenol and 1 mM glucose had been added. After shake-culturing for 3 days at 30° C. and collecting the microbial cells from the culture liquid by centrifugation, the cells were resuspended in adequate volume of NMS medium not containing phenol, and the amount of inoculated cells in the above-mentioned vials was $10^8$ to $10^9$ cells/g and the moisture content after addition of the suspension was 25%. After capping the vials with screw-on caps wrapped with Teflon-coated packings and shaking, the vials were incubated for 7 days at 30° C.

Figure 4:
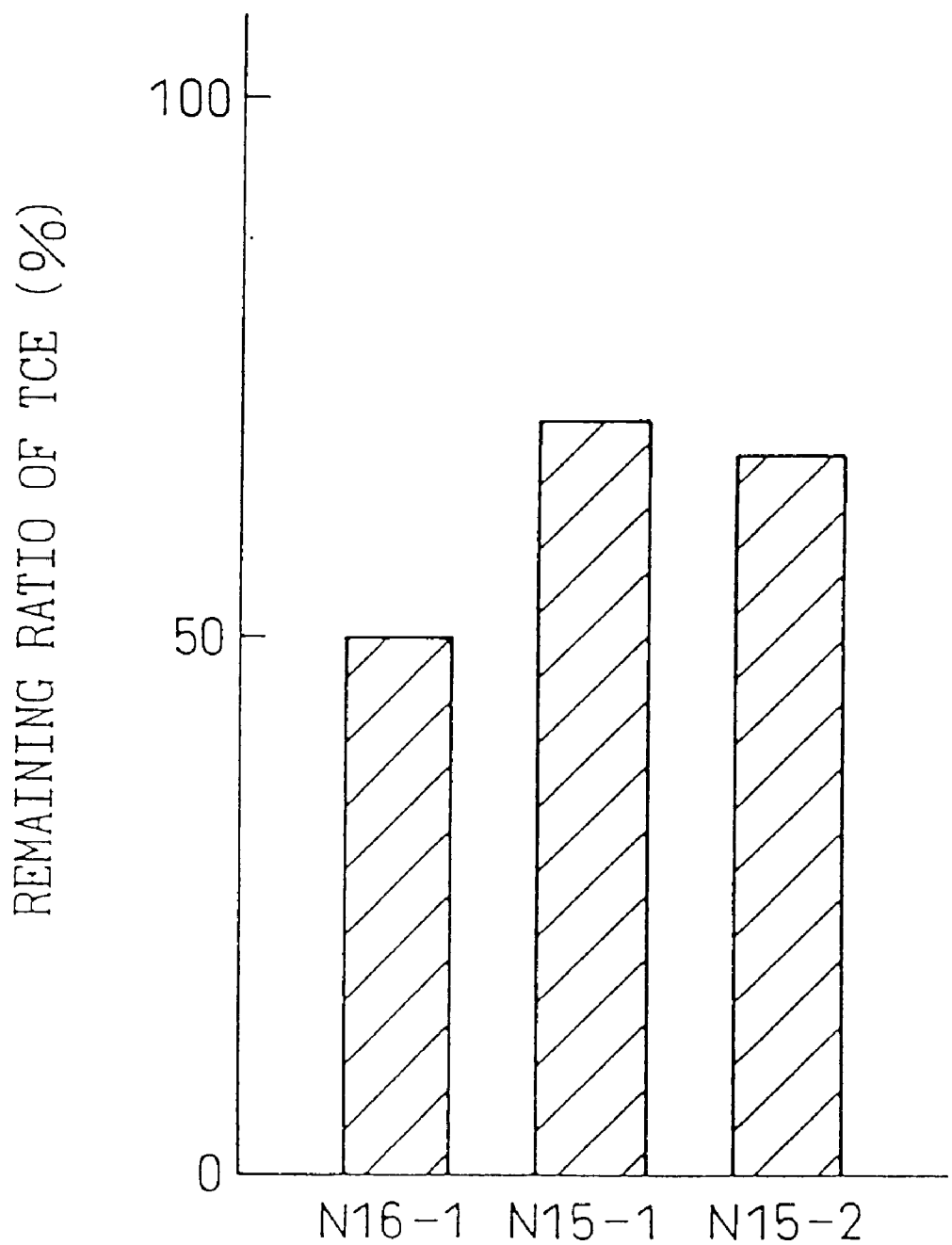
FIG. 4 is a graph indicating the percentage of remaining TCE in Example 6.

10 g of the soil were weighed in an Erlenmeyer flask provided with a stopper followed by the addition of 90 ml of ion exchange water aerated with air passed through activated charcoal, 5 ml of phosphoric acid and 10 ml of n-hexane. After sealing the flask, ultrasonic treatment was performed for 20 minutes in an ultrasonic cleaner followed by shaking for 5 minutes with a shaker. Next, the aqueous phase and n-hexane phase were transferred to a colorimetric tube provided with a stopper. After sealing the colorimetric tube and performing ultrasonic treatment, the separated n-hexane was analyzed by gas chromatography. Those results are shown in FIG. 4.

30 to 50% of the TCE at an initial concentration of 10 ppm was decomposed in 7 days. Thus, the microorganisms of the present invention demonstrated decomposing ability even in a natural environment. Accordingly, it is possible clean contaminated soil by bringing the soil in contact with the microorganisms of the present invention and water. In addition, this technique enables soil to be cleaned without adding activator compounds such as phenol directly to the soil.

Example 8. Decomposition Test of TCE in Soil 10 g of Andsols (sampled from Aichi prefecture and air dried) were placed in a vial having a volume of 30 ml followed by the addition of TCE to a concentration of 20 ppm. Strains N15-1, N15-2 and N16-1 were each inoculated into 20 ml of NMS liquid medium to which 0.02% yeast extract, 500 ppm phenol and 1 mM glucose had been added, followed by shake-culturing for 1 day at 30° C.

Figure 5:
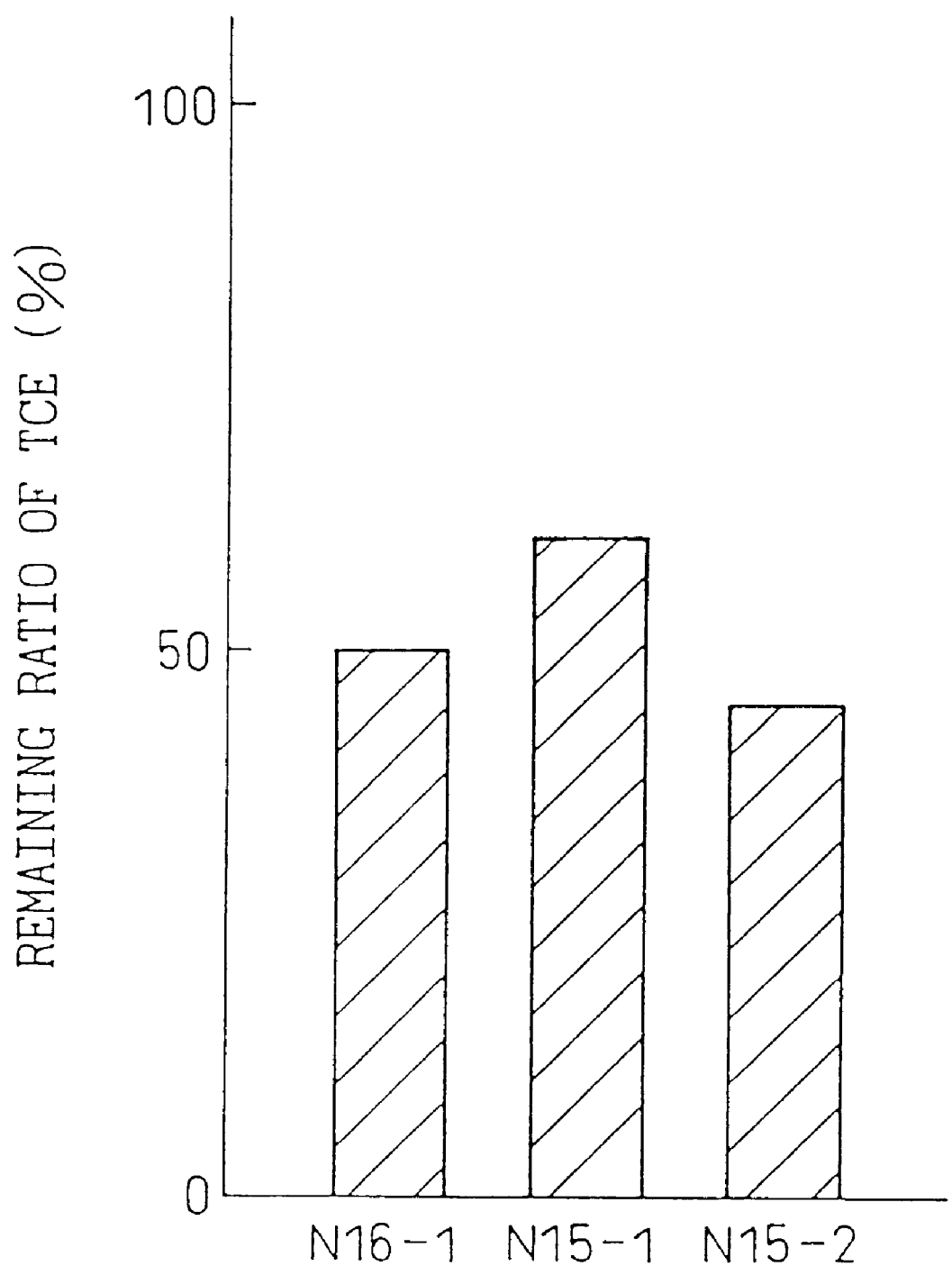
FIG. 5 is a graph indicating the percentage of remaining TCE in Example 7.

0.2 ml of this liquid was removed and added to the above-mentioned vial so that the amount of inoculated microbial cells was $10^6$ cells/g, the moisture content following addition of medium was 40% and phenol concentration was 500 ppm. After capping the vial with a screw-on cap wrapped with a Teflon-coated packing and shaking, the culture liquid was cultured for 3 weeks at 30° C. Those results are shown in FIG. 5. 40 to 50% of the TCE was decomposed, thus indicating that the microorganisms of the present invention are able to decompose TCE in soil taken from a natural environment even at a low concentration of $10^6$ cells/g.

Example 9. Induction of Decomposition Activity by an Activator

Strains N15-1, N15-2 and N16-1 were each cultured for 2 days at 30° C. in 5 ml of NMS liquid medium in which 0.2% yeast extract and 5 mM glucose had been added. 4 ml of NMS liquid medium to which 0.02% yeast extract, 1 mM glucose and one of the activators listed in Table 4 at a concentration of 100 ppm had been added were placed in vials that were then inoculated with 40 µl of each of the above-mentioned culture liquid (microorganism count of approximately $10^6$ cells/g). 30 ppm TCE was then added to each vial followed by promptly sealing the vials with a Teflon-coated silicon septum and an aluminum cap. The vials were cultured with shaking for 5 days at 30° C. and the vapor phase was analyzed by gas chromatography. The result is shown in Table 5. The numbers shown indicate the concentration of remaining TCE during addition of the microorganisms as a percentage when the concentration of TCE when microorganisms are not added is taken to be 100%. Those results are shown in the following Table 3.

TABLE 3

| | Microorganism Strain | | |
|---|---|---|---|
| Compound | N16-1 | N15-1 | N15-2 |
| Cyclohexanol | 8.6 | 57.4 | 64.1 |
| Cyclopentanol | 49.3 | 100 | 100 |
| Anthranilic acid | 13.3 | 105 | 107 |
| Caffeinic acid | 52.6 | 96.7 | 102 |
| Suberinic acid | 7.3 | 99.8 | 100 |
| Maleic acid | 53.0 | 100 | 98.8 |
| Fumaric acid | 63.4 | 100 | 100 |
| Succinic acid | 63.3 | 72.4 | 92.4 |
| Malonic acid | 45.2 | 100 | 100 |
| Trans-3-hexenoic acid | 2.7 | 100 | 100 |
| Hexanoic acid | 8.3 | 100 | 100 |
| Benzene | 0 | 98.8 | 97.3 |
| Ethylbenzene | 28.7 | 98.4 | 101 |
| Benzyl alcohol | 0 | 71.9 | 72.5 |
| Saligenin | 0 | 102 | 105 |
| Allylphenol | 0.5 | 100 | 102 |
| Guaiacol | 35.0 | 99.2 | 107 |
| Toluene | 0 | 100 | 100 |
| Benzaldehyde | 6.8 | 103 | 99.0 |
| p-hydroxybenzoic acid | 12.5 | 102 | 98.8 |

N15-1 and N15-2 were activated by aromatic compounds such as phenol, toluene and benzene, which are known to be conventional activation inducers, as well as by the non-aromatic compound, cyclohexanol. In addition, succinic acid also exhibited the ability to activate these microorganisms. Moreover, N16-1 was also activated by cyclopentanol, anthranilic acid, p-hydroxybenzoic acid, suberinic acid, trans-3-hexenoic acid and straight chain carboxylic acids such as hexanoic acid.

Furthermore, a comparison of the properties of strains N15-1, N15-2 and N16-1 of the present invention with those of known *Burkholderia cepacia* strains KK01 and G4 is shown in the following Table 4.

TABLE 4

| | Burkholderia cepacia | | | Burkholderia genus |
|---|---|---|---|---|
| Property | KK01 | G4 | N15-1,2 | N16-1 |
| Decomposing abiiity | 30→15/2 days, organism count unknown | 1→0.17/1 day, 3 × $10^8$ cells/ml | 100→40/2 days, $10^8$ cells/ml | 100→45/day, $10^8$ cells/ml |
| Max. TCE conc. | 30 (ppm) | 2 | 100 | 100 |
| Activators | Toluene, phenol, cresol | Toluene, phenol, cresol | Not toluene, phenol cresol, cyclohexanol | Toluene, cresol, cyclohexanol suberinic acid, others |
| Mobility | + | − | + | + |

According to the present invention, the microorganisms of the present invention are able to decompose high concentrations of halogenated hydrocarbons such as TCE and DCE contained in water or soil in the presence of preferably at least one type of activator and sugar or other nutrient.

According to the process for purifying water or soil in the present invention, in addition to offering the advantages of biotechnology such as not requiring a large amount of energy and inhibiting the occurrence of secondary contamination, the process of the present invention is able to industrially and efficiently purify water or soil contaminated by halogenated hydrocarbons in the natural environment.

Example 10. Decomposition of Trichloroethylene in Liquid Culture

The strains N15-1, N15-2 and N16-1 were separately cultured in a liquid NMS medium supplemented with 0.2% yeast extract and 5 mM glucose for one day. 4 ml of liquid NMS medium supplemented with 0.02% yeast extract, 100 ppm phenol and 1 mM glucose was put into each vial, and 40 µl of the culture as prepared above was inoculated into the vials (about $10^6$ cells/ml medium). Trichloroethylene was added to vials to make a concentration of 30 ppm, and the vials were rapidly shielded with a Teflon-coated silicone plug and aluminum cap. The vials were incubated at 30° C. with shaking, and the gas phase in the vials was periodically analyzed by gas chromatography. As a result, 100% trichloroethylene was decomposed in 18 hours.

We claim:

1. Microorganism belonging to the genus Burkholderia and having an ability to decompose halogenated hydrocarbon, which are able to decompose 50% or more of 100 ppm of trichloroethylene in 2 days, or to decompose 100% of 30 ppm of trichloroethylene in 18 hours.

2. Microorganism according to claim 1 wherein said halogenated hydrocarbon is trichloroethylene.

3. Microorganism according to claim 1 that are Burkholderia N16-1 (FERM BP-5504).

4. Microorganism according to claim 1 that are *Burkholderia cepacia* N15-1 (FERM BP-5502).

5. Microorganism according to claim 1 that are *Burkholderia cepacia* N15-2 (FERM BP-5503).

6. A process for cleaning water or soil containing halogenated hydrocarbon comprising adding to said water or soil a microorganism belonging to the genus Burkholderia and having an ability to decompose 50% or more of 100 ppm of trichloroethylene in two days or 100% of 30 ppm trichloroethylene in eighteen hours.

7. A process according to claim 6 wherein a microorganism activator is added to the water or soil with said microorganism.

8. A process for cleaning water or soil containing halogenated hydrocarbon comprising adding to said water or soil a microorganism selected from *Burkholderia cepacia* N-15-1 (FERM BP 5502) and *Burkholderia cepacia* N-15-2 (FERM BP 5503), said microorganism having the ability to decompose halogenated hydrocarbon.

9. A process according to claim 7 wherein the microorganism activator is selected from the group consisting of cyclohexanol, cyclopentanol, anthranilic acid, caffeinic acid, suberinic acid, maleic acid, fumaric acid, succinic acid, malonic acid, trans-3-hexanoic acid, hexanoic acid, benzene, ethylbenzene, benzylalcohol, saligenin, allylphenol, guaiacol, toluene, benzaldehyde, p-hydroxybenzoic acid and combinations thereof.

* * * * *

UNITED STATES PATENT AND TRADEMARK OFFICE
CERTIFICATE OF CORRECTION

PATENT NO. : 5,998,198
DATED : 7 December 1999
INVENTOR(S) : Mika NAKAYAMA et al.

It is certified that error appears in the above-identified patent and that said Letters Patent is hereby corrected as shown below:

| Column | Line | |
|---|---|---|
| 2 | 20 | Change "*tricosiorium*" to --*tricosporium*--. |
| 2 | 38 | Change "*aenes eutronus*" to --*genes eutropus*--. |
| 2 | 39 | Change "*Alcaliaenes*" to --*Alcaligenes*--. |
| 2 | 49 | Change "*Alcaliaenes*" to --*Alcaligenes*--. |
| 3 | 33 | Change "change-over" to --change over--. |
| 4 | 67 | Change "from-the" to --from the--. |
| 6 | 53 | After "does" delete "a". |
| 8 | 55 | After "possible" insert --to--. |
| 10 | 17 | Change "conc.     (ppm)" to --conc.(ppm)--. |

Signed and Sealed this

Seventeenth Day of April, 2001

Attest:

NICHOLAS P. GODICI

*Attesting Officer*         *Acting Director of the United States Patent and Trademark Office*